(12) United States Patent
Goerlach-Graw et al.

(10) Patent No.: US 7,267,992 B2
(45) Date of Patent: Sep. 11, 2007

(54) METHOD FOR THE DETERMINATION OF AN ANALYTE IN A LIQUID

(75) Inventors: Ada Goerlach-Graw, Grosskarlbach (DE); Reiner Schlipfenbacher, Bad Duerkheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 11/348,705

(22) Filed: Feb. 7, 2006

(65) Prior Publication Data
US 2006/0128029 A1    Jun. 15, 2006

Related U.S. Application Data

(62) Division of application No. 09/594,972, filed on Jun. 15, 2000, now Pat. No. 7,026,002.

(30) Foreign Application Priority Data
Jun. 18, 1999    (DE) ............................. 199 27 783

(51) Int. Cl.
*G01N 33/53* (2006.01)
(52) U.S. Cl. ............ 436/514; 436/528; 436/518; 436/161; 436/810; 435/7.1; 435/7.2; 435/7.94; 435/970; 435/287.1; 435/287.2; 435/969; 435/975
(58) Field of Classification Search ................ 436/514, 436/528, 161; 435/7.1, 7.2, 7.94, 970, 969, 435/975, 287.1, 287.2
See application file for complete search history.

(56) References Cited
U.S. PATENT DOCUMENTS 4,230,683 A    10/1980 Decker et al.
4,515,889 A    5/1985  Klose et al.

(Continued)

FOREIGN PATENT DOCUMENTS

DE    198 38 802 A    12/1999

(Continued)

OTHER PUBLICATIONS

Schlipfenbacher R L et al. "Immunometric Dipstick for Rapid and Simple Screening of Microalbuminuric Patients", Clinical Chemistry, Bd. 36, Nr. 6, 1990 (1pp).

(Continued)

*Primary Examiner*—Bao-Thuy L. Nguyen
(74) *Attorney, Agent, or Firm*—Jill L. Woodburn; Brian Smiler

(57) ABSTRACT

A method is provided to determine the presence of an analyte in a sample. The method provides an element with a sample application zone, a detection zone, a zone containing immobilized analyte or analyte analogue, a conjugate that has a first bioaffine binding partner capable of a specific binding reaction with the analyte and a first detectable label, and a universal conjugate, which can be detached by liquid and comprises a second bioaffine binding partner and a visually detectable label. The second bioaffine binding partner is capable of a specific binding reaction with the first detectable label. The method also includes contacting the sample application zone with the sample, contacting the sample with the conjugate and the universal conjugate to react the analyte with the and the universal conjugate to form a detection complex, and determining the presence of the detection complex in the detection zone of the element.

9 Claims, 1 Drawing Sheet

U.S. PATENT DOCUMENTS

| | | |
|---|---|---|
| 4,861,711 A | 8/1989 | Friesen et al. |
| 5,118,609 A | 6/1992 | Baier et al. |
| 5,160,486 A | 11/1992 | Schlipfenbacher et al. |
| 5,268,306 A | 12/1993 | Berger et al. |
| 5,451,504 A | 9/1995 | Fitzpatrick et al. |
| 5,478,752 A | 12/1995 | Lerch et al. |
| 5,516,635 A | 5/1996 | Ekins et al. |
| 5,591,645 A | 1/1997 | Rosenstein |
| 5,662,911 A | 9/1997 | Huber et al. |
| 5,824,268 A | 10/1998 | Bernstein et al. |
| 5,874,216 A | 2/1999 | Mapes |
| 5,977,296 A | 11/1999 | Nielsen et al. |
| 6,357,163 B1 | 3/2002 | Buchardt et al. |
| 6,395,474 B1 | 5/2002 | Buchardt et al. |
| 6,472,226 B1 | 10/2002 | Barradine et al. |
| 6,514,773 B1 | 2/2003 | Klein et al. |
| 6,703,196 B1 | 3/2004 | Klepp et al. |
| 6,710,163 B1 | 3/2004 | Buchardt et al. |

FOREIGN PATENT DOCUMENTS

| | | |
|---|---|---|
| EP | 0 291 194 B1 | 11/1988 |
| EP | 0 291 194 B2 | 11/1988 |
| EP | 0 291 194 B8 | 11/1988 |
| EP | 0 331 127 B1 | 9/1989 |
| EP | 0 571 941 B1 | 12/1993 |
| EP | 0 585 912 B1 | 3/1994 |
| EP | 0 267 521 A2 | 5/1998 |
| EP | 0 267 521 A3 | 5/1998 |
| GB | 2 342 992 A | 4/2000 |
| WO | 97/06439 | 2/1997 |

OTHER PUBLICATIONS

Frens, G. "Controlled Nucleation for the Regulation of the Particle Size in Monodisperse Gold Suspensions", Nature Physical Science vol. 241 Jan. 1, 1973 pp. 20-22.

J. Roth "The Colloidal Gold Marker System for Light and Electron Microscopic Cytochemistry" in Bullock, G.R. and Petrurz, P. (eds.), "Techniques in Immunocytochemistry", vol. 2, Academic Press, New Yor 1983, 216-284.

METHOD FOR THE DETERMINATION OF AN ANALYTE IN A LIQUID

REFERENCE TO RELATED-APPLICATIONS

The present application is a divisional application claiming priority to U.S. patent application Ser. No. 09/594,972, filed on Jun. 15, 2000 now U.S. Pat. No. 7,026,002 and also claims priority to under 35 U.S.C. §119 of German Application Serial No. 199 27 783.4 filed Jun. 18, 1999, each of which is hereby incorporated by reference.

TECHNICAL FIELD

The invention concerns an element for the determination of an analyte in a liquid by means of a specific binding reaction of two bioaffine binding partners containing in or on material which enables liquid transport between zones, a sample application zone and a detection zone located downstream thereof and a zone containing immobilized analyte or analyte analogue between the sample application zone and detection zone, and impregnated conjugate that can be detached by liquid and is located in the sample application zone or upstream or downstream thereof composed of a bioaffine binding partner capable of a specific binding reaction with the analyte to be determined and a detectable label.

BACKGROUND

Such elements are known for example from DE-A3842702 or DE-A4439429. The described analytical elements contain the necessary reagents to carry out immunoenzymometric or immunoenzymometric-like methods of determination. In particular these are analyte or analyte analogue immobilized in a zone, between the sample application zone and detection zone and a conjugate composed of a bioaffine binding partner capable of a specific binding reaction with the analyte to be determined and a detectable label.

In the case of DE-A 3842702 an enzyme label is described as the detectable label. In order to make this label visible it is necessary to contact it with a chromogenic enzyme substrate such that a colour is formed as a result of the enzymatic activity. The requirement that the label has to be made visible is a complication, costly due to the measures that have to be taken and furthermore may result in technical difficulties for example when the corresponding enzyme substrate has stability problems in the analytical element.

Therefore recently direct labels have been preferred as described in DE-A 4439429. These direct labels are for example metal or latex particles which have an intrinsic colour and can be visualized with the naked eye. Nowadays a gold label is particularly preferred. For this an appropriately labelled bioaffine binding partner depending on the analyte is prepared for which optimal conditions then have to be created on the analytical element for reaction and storage. This individual adaptation to the analyte to be determined is very laborious. Depending on the analyte to be determined, the required polyclonal or monoclonal antibodies can behave very differently when conjugated to gold particles. This can lead to different stabilities of gold conjugates. The differences in the behaviour of the various polyclonal antibodies or various monoclonal antibodies when coated on gold particles can result in quite different spatial arrangements of the antibodies on the gold particles which leads to steric problems when such conjugates are reacted with the analyte and can thus result in a poor sensitivity.

SUMMARY

The present invention provides an analytical element containing stable reagents that can be produced simply and reproducibly and which enables a sensitive determination reaction.

The invention concerns an element for the determination of an analyte in a liquid by means of a specific binding reaction of two bioaffine binding partners containing in or on material which enables liquid transport between zones, a sample application zone and a detection zone located downstream thereof as well as a zone containing immobilized analyte or analyte analogue between the sample application zone and detection zone and an impregnated conjugate 1 upstream of the zone containing immobilized analyte or analyte analogue that can be detached by liquid and is composed of a bioaffine binding partner 1 capable of a specific binding reaction with the analyte to be determined and a detectable label 1, characterized in that the detectable label 1 is a low molecular organic molecule and a universal conjugate 2 is present upstream of the zone containing immobilized analyte or analyte analogue which can also be detached by liquid and is composed of a bioaffine binding partner 2 capable of a specific binding reaction with the detectable label 1 and a visually detectable label 2.

The invention additionally concerns the use of an element according to the invention to determine an analyte and a corresponding method of determination. This method for the determination of an analyte by means of an element according to the invention is characterized in that a sample application zone is contacted with analyte, the analyte is moved by liquid towards the detection zone, analyte present in this liquid reacts with conjugates 1 and 2 to form a detection complex, the detection complex is transported by liquid into the detection zone and is determined there.

Finally the invention concerns a kit for the determination of an analyte containing an analytical element according to the invention and an elution agent.

DETAILED DESCRIPTION

Figure 1:
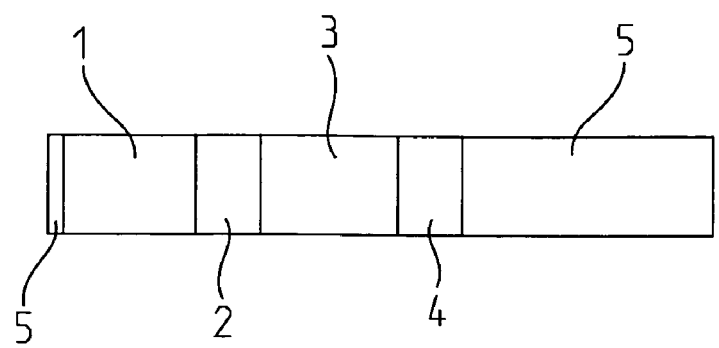
FIG. 1 is a top view of an element according to the invention.

The determination of an analyte by means of an element according to the invention is based on a specific binding reaction of two bioaffine binding partners. Bioaffine binding partners and corresponding specific binding reactions between the binding partners are known to a person skilled in the art. Bioaffine binding partners are for example hapten and antibody, antigen and antibody, lectin and sugar or saccharide, avidin or streptavidin and biotin as well as nucleic acid and nucleic acid, ligand and receptor. In this case an antigen can be any molecule against which it is experimentally possible to produce antibodies. An antigen can also be an antibody or a particular site on an antibody which is referred to as an epitope and which can be specifically recognized and bound by an antibody. Nucleic acids are to be understood as all possible forms of nucleic acids which are able to bind by means of complementary bases. Special mention is made of DNA, RNA and also nucleic acid analogues such as peptide nucleic acids (PNA, see for example WO 92/20702) which is not to be regarded as a definitive list. Ligand and receptor refer quite generally to a specific binding interaction between two partners such as between a hormone and hormone receptor.

The element according to the invention contains the reagents required to carry out the determination of an analyte and other zones necessary for the function of the element in or on material which enables a liquid transport. It is important for the analytical element according to the invention that liquid can move within the element towards the detection zone. Such a liquid flow is for example possible in a suitably prepared hollow body by means of gravitational force. Devices which enable liquid transport by centrifugal force as one form of gravitational force are for example known from EP-B 0052769. However, analytical elements according to the invention can contain absorbent materials that can move liquid by capillary force. The materials of the individual zones of the element according to the invention can be the same or different. It will frequently be the case that different zones are composed of different materials if these are to optimally fulfil their function.

Basically all materials are potentially suitable as absorbent capillary active materials which can be generally used for liquid uptake in so-called "dry tests" as described for example in U.S. Pat. No. 4,861,711, U.S. Pat. No. 5,591,645 or EP-A 0291194 or in DE-A 3842702 or DE-A 4439429. For example porous materials have proven to be advantageous for this purpose such as membranes e.g. nitrocellulose membranes. However, it is also possible to use fibrous absorbent matrix materials such as fleeces, fabrics or knitted fabrics. Fleeces are particularly preferred. Fibrous matrix materials can contain glass, cellulose, cellulose derivatives, polyester, polyamide and also viscose, synthetic wool and polyvinyl alcohol. Fleeces made of fibres based on cellulose, polymer fibres based on polyester and/or polyamide and an organic binder as OH and/or ester groups as known from EP-B 0326135 can for example be used in the invention. Fleece materials containing meltable copolyester fibres in addition to glass fibres, polyester fibres, polyamide fibres, cellulose fibres or cellulose derivative fibres as described in the European Patent Application 0571941 can also be used in analytical elements according to the invention. Papers such as tea bag paper can also be readily used.

In order to improve the handling of the analytical element according to the invention the absorbent capillary-active material or various absorbent capillary-active materials can be arranged on a rigid support material which in turn is not permeable to liquid, does not adversely affect the liquid flow in the matrix material and is inert with regard to the reactions which occur in the analytical element. A support material can for example be a polyester foil onto which the matrix material enabling liquid transport is attached.

The individual zones in the element according to the invention can be arranged above one another, adjacent to one another, or partially above one another and partially adjacent to one another on the support material. An analytical element according to the invention is provided in which the sample application zone, the zone containing immobilized analyte or analyte analogue and detection zone are arranged adjacent to one another on the support material. In this connection adjacent to one another means that the zones are in direct contact with one another in the direction of liquid transport or are essentially disposed in one plane separated by other zones.

The sample application zone is the region of the element according to the invention on which the sample is applied in which it is intended to determine whether a particular analyte is present or, optionally, in which quantity it is present.

The detection zone is the region of the analytical element according to the invention in which it is determined whether the examined analyte was present in the sample applied to the element. This determination can be qualitative, semi-quantitative or quantitative. In this connection semi-quantitative means that no definite concentration value is determined for the analyte but rather a concentration range in which the analyte concentration is present.

According to the invention a zone containing immobilized analyte or analyte analogue is located between the sample application zone and detection zone. In this connection analyte analogue is understood as a substance which behaves comparably to the analyte to be determined with regard to a specific binding reaction with the bioaffine binding partner.

The analyte or analyte analogue can be immobilized on a matrix material between the sample application zone and detection zone by methods known to a person skilled in the art. Thus it is for example possible to adsorb the analyte or analyte analogue onto a suitable matrix material in such a manner that the analyte or analyte analogue is not detached by liquid under the test conditions. Of course the immobilization can also be by chemical means with formation of covalent bonds. An analyte can be immobilized on the matrix material either directly or via a spacer. In the case of a spacer the analyte is usually chemically modified with a suitable spacer and then this analyte analogue is bound to the matrix material. However, an indirect binding of the analyte or analyte analogue to the matrix material can also be achieved by means of two bioaffine binding partners such as biotin and streptavidin.

Polyhaptens have proven to be particularly suitable as an analyte analogue when detecting haptens. Polyhaptens are substances which have a plurality of haptens so that a plurality of bioaffine binding partners can be specifically bound thereto. Due to the high density of bioaffine binding partners that can be achieved in this manner it is possible to attain a high test sensitivity.

The invention requires the presence of two conjugates on the element. These conjugates can be located in the sample application zone. They can also be arranged upstream or downstream of the sample application zone. The conjugates can be impregnated in the suitable matrix material. But they can also be coated on the matrix material. Conjugates 1 and 2 can be present as a mixture. But they can also be arranged separately and then do not have to also necessarily be located directly next to one another. In the latter case it is then also possible that for example one conjugate is located upstream of the sample application zone and the other conjugate is for example located in a zone between the sample application zone and the zone containing the immobilized analyte or analyte analogue.

Conjugate 1 is composed of a bioaffine binding partner 1 capable of a specific binding reaction with the analyte to be determined and a detectable label 1. If the analyte to be determined is a hapten or an antigen, the bioaffine binding partner 1 is an antibody which can undergo a specific binding reaction with the analyte. If the analyte is an antibody, the bioaffine binding partner 1 can be a corresponding hapten or antigen which can undergo a specific binding reaction with the antibody.

The detectable label 1 is understood according to the invention as a low molecular organic molecule, preferably an organic molecule with a molecular weight of less than 1,500, particularly preferably of less than 1,000 which as a hapten can be bound by an appropriate antibody in a specific binding reaction and can thus be detected. Digoxigenin or digoxin have proven to be excellently suitable for this purpose. Digoxin is quite especially preferred.

The label 1 is preferably bound covalently to the bioaffine binding partner 1. Such conjugates can be reproducibly prepared by simple organic-chemical reactions.

Conjugate 2 is, depending on the analyte to be de>ermined, a conjugate that can be used universally composed of a bioaffine binding partner 2 capable of a specific binding reaction with the detectable label 1 and a visually detectable label 2. The bioaffine binding partner 2 is particularly preferably an antibody against the low molecular organic molecule used as the label 1. So-called direct labels are preferably used as the visually detectable label 2 i.e. labels which can be recognized by the eye as a result of their colour without further handling steps. Advantageous labels of this type are for example particles that are insoluble in water such as metal or latex particles and also pigments such as silicate, carbon black or selenium. In particular metal particles are preferably used according to the invention as a label. Colloidal gold is particularly preferred as a label. The label 2 can be bound covalently or adsorptively to the bioaffine binding partner 2 whereby adsorptively includes all possibilities apart from covalent binding. In the case of colloidal metals as direct labels, in particular colloidal gold, adsorptive bonds are preferably utilized.

It is important for the invention that both conjugates are located in or on the matrix material upstream of the zone containing immobilized analyte or analyte analogue in such a way that they can be detached by liquid and transported towards the detection zone.

According to the invention both conjugates or only one of the conjugates can be located upstream of the sample application zone in the element according to the invention. In this case it is necessary that an elution agent application zone is also located upstream of the sample application zone. In this case it is necessary that after sample containing analyte has been applied to the sample application zone, the conjugate/the conjugates is/are transported by an additionally applied elution agent through the sample application zone towards the detection zone. In this case water or suitable aqueous solutions such as buffers are suitable as elution agents.

In an alternative embodiment of the analytical element according to the invention an elution agent application zone separate from the sample application zone is not provided. This is adequate when the sample application zone is arranged upstream of the zone or zones containing the conjugates, of the zone containing immobilized analyte or analyte analogue and of the detection zone.

It is also possible that an elution agent application zone is located upstream of the sample application zone either on separate matrix materials or on the same matrix material.

Use of two conjugates as described above in an element according to the invention for the determination of an analyte has considerable advantages compared to the prior art embodiments. Thus the universal conjugate 2 is a stable conjugate composed of a visually detectable label and a bioaffine binding partner which has a high sensitivity towards a low molecular organic molecule. Conjugate 2 can be produced reproducibly. The use of a low molecular organic molecule as a detectable label 1 enables polyclonal antibodies or monoclonal antibodies to be conjugated reproducibly, simply and in the same quality by chemical methods. In this manner defined products are produced. In immunoassays with labelled binding partners of the analyte the labelled binding partner is usually a critical component. Optimization work especially with regard to the storage life of the components on the analytical element and already before processing and the sensitivity of these components is not necessary with the present invention or is at least considerably simplified. This also applies to the optimization of reaction conditions on the analytical element and the ability to elute the conjugate in the analytical element which can be largely standardized. This work is mainly limited only to conjugate 1 which, due to the nature of its components, can be much more simply optimized than a conjugate composed of a bioaffine binding partner which varies according to the analyte and a visually detectable label which are often both very heterogeneous and cannot be determined exactly and thus with reference to the product are difficult to produce in the same reproducible quality.

An analyte is determined using an element according to the invention in such a way that the sample which is to be examined for the presence of analyte is contacted with the sample application zone. Either the analyte is itself already dissolved or suspended in liquid or additional liquid is applied to the element as an elution agent in order to transport the constituents of the sample, especially the analyte which may be present, with liquid towards the detection zone. The analyte present in the sample thereby comes into contact with the mixture of conjugates 1 and 2 and reacts with them to form a detection complex. This detection complex is transported with the liquid into the detection zone and is determined there. Only if analyte was present in the sample does visually detectable label 2 reach the detection zone in the form of the previously mentioned complex and can be detected there. If no analyte was present in the examined sample, the mixture of conjugates 1 and 2 is bound in the zone containing immobilized analyte or analyte analogue and no visually detectable label 2 reaches the detection zone. In order to function optimally, conjugate 1 as well as conjugate 2 are present at such a concentration that the analyte or the analyte analogue immobilized in the zone between the sample application zone and detection zone is able to completely bind the conjugates. Conjugates and correspondingly also the immobilized analyte or the immobilized analyte analogue should be present in an excess relative to the analyte to be determined. In an embodiment conjugate 1 is present in an excess relative to conjugate 2 because a particularly high sensitivity is achieved. A six- to ten-fold excess of conjugate 1 relative to conjugate 2 has proven to be particularly advantageous.

If it is intended to transport the sample through the element according to the invention into the detection zone using an additional elution agent, a kit has proven to be advantageous which is composed of the analytical element according to the invention and a corresponding elution agent. In this case the elution agent can be water or an aqueous solution, preferably a buffer solution and the elution agent is in a suitable container. This container can for example be a dropping bottle in order to apply the liquid to the elution agent application zone. It can, however, also for example be a cup which is closed with a cap when not in use and can be de-capped to carry out the method of determination, and an element according to the invention can be placed in the cup containing the elution agent liquid in such a manner that elution agent is taken up via the elution agent application zone and migrates through the various zones into the detection zone.

A top-view of four different possible embodiments of an element according to the invention is shown in FIG. 1-4.

An embodiment of an element according to the invention is shown in FIG. 1. Matrix materials (1-4) are attached side by side on a rigid inert support foil (5) in such a manner that their ends butt or slightly overlap. The matrix materials (1-4) represent the test zones of the analytical element according to the invention. They are preferably composed of different absorbent materials (papers, fleeces, porous plastic layers and such like) and liquid contact at the abutting edges is achieved by sufficiently close adjoining of the layers. However, in an alternative embodiment it is of course also possible that several adjacent zones are made in one piece or several pieces from the same material. Overall the test zones form a liquid transport path which leads from the sample application zone (1) through the conjugate zone (2) containing conjugate 1 and conjugate 2 and the capture zone (3) containing immobilized analyte or analyte analogue into the detection zone (4). The conjugates 1 and 2 can be applied together in the conjugate zone (2) after prior mixing of suitable solutions or suspensions. The conjugate zone (2) can also be firstly impregnated with one conjugate and then reimpregnated with the other conjugate. Or the conjugate zone (2) can contain two identical or different matrix materials laying on top of one another each of which carries a different conjugate.

In the present case the analytical element is one in which either sufficient liquid sample is applied that the liquid volume is adequate to supply all matrix materials including the detection zone (4) with liquid or in which firstly sample is applied to the sample application zone (1) which is then subsequently transported through the element according to the invention by a special elution agent which is also applied to the sample application zone (1). In the case of a sample containing analyte a detection complex composed of analyte and conjugates 1 and 2 is formed from conjugate zone (2) onwards as the analyte is transported with liquid through the various zones (1-4). This complex migrates through the capture zone (3) and reaches the detection zone (4) where for example a gold label serving as the label 2 is detectable by eye as a red colouration. When the sample contains no analyte, during liquid transport through the zones (1-4) of the element according to the invention, the conjugates are transported from the conjugate zone (2) into the capture zone (3) where the conjugate mixture is bound to the immobilized analyte or analyte analogue. Visually detectable label 2 does not reach the detection zone (4) in this case. No colouration will be detectable there.

Figure 2:
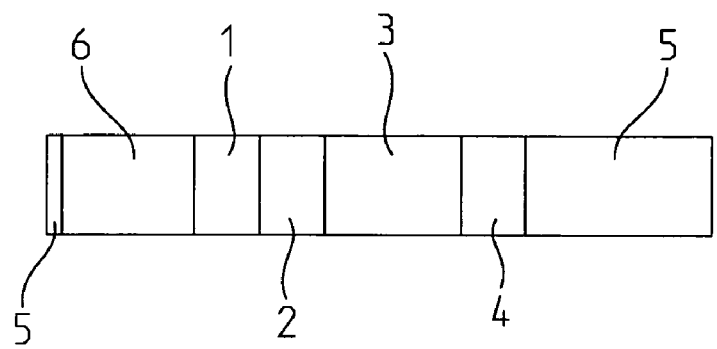
FIG. 2 is a top view of an element according to the invention.
Figure 3:
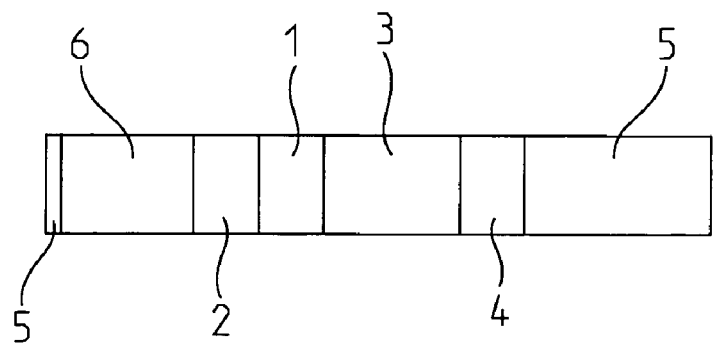
FIG. 3 is a top view of an element according to the invention.

Elements according to the invention are shown in FIGS. 2 and 3 in which an elution agent application zone (6) is placed in front of the sample application zone (1). When using such elements the sample is firstly applied to the sample application zone (1). Subsequently sufficient elution agent is applied to the elution agent application zone (6) that analyte is transported into the conjugate zone (2) where it can form a complex with conjugates 1 and 2 and the complex that is formed reaches the detection zone (4) via zone (3) containing immobilized analyte or analyte analogue where the analyte is detected.

However, the elution agent application zone (6) of the elements of FIG. 2 or 3 can be placed in so much elution agent that the sample application zone (1) in the case of an element of FIG. 2 or the conjugate zone (2) in the case of an element of FIG. 3 is located above the liquid level of the elution agent.

Whereas in FIG. 2 the sequence of zones (1-4) is the same as in the element of FIG. 1, the sequence of the sample application zone (1) and conjugate zone (2) in the element of FIG. 3 is interchanged. In this case the elution agent firstly comes into contact with conjugates 1 and 2 and preincubates these before the analyte is contacted and bound.

Figure 4:
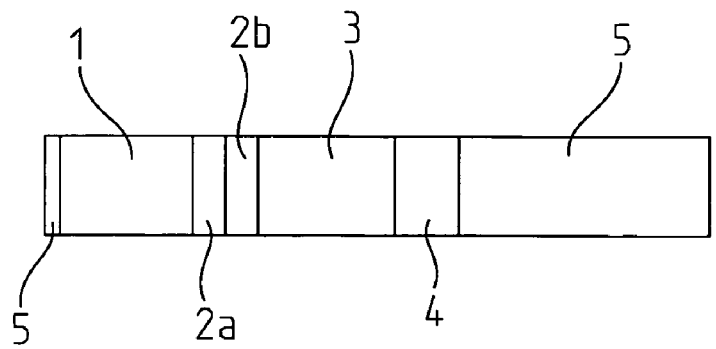
FIG. 4 is a top view of an element according to the invention which contains two adjacent zones, which each carry a different one of two conjugates.

FIG. 4 shows an element according to the invention which contains two adjacent zones 2a and 2b which each carry a different one of the two conjugates 1 and 2. In this case the conjugates can be located on the same one-piece or two-piece matrix material or they can be present on different types of matrix materials. The sequence of zones (1), (3) and (4) relative to one another and relative to the conjugate zone which is divided into the partial regions 2a and 2b is identical to that show in FIG. 1. The function of the element of FIG. 4 therefore corresponds to that described for the element of FIG. 1 except that the conjugates 1 and 2 are dissolved successively.

The invention is elucidated in more detail by the following example.

EXAMPLE 1

Determination of Benzodiazepine Using an Element According to FIG. 1

A. Preparation of a Conjugate Composed of Gold and Monoclonal Antibody to Digoxin Two conjugates are prepared. Conjugate A contains gold particles with a size of approximately 40 nm, loaded with an antibody concentration of 2 mg/l. Conjugate B contains gold particles with a size of ca. 20 nm, loaded with an antibody concentration of 10 mg/l.

Gold sol with an average particle diameter of ca. 40 nm and ca. 20 nm was prepared according to the method of Frens (Frens, G., "Preparation of gold dispersions of varying particle size: Controlled nucleation for the regulation of the particle size in monoodisperse gold suspensions" in Nature: Physical Science 241 (1973), 20-22) by reducing a 0.01 percent by weight tetrachloroauric acid solution with trisodium citrate while boiling.

The antibody-gold conjugate preparation is based on the method of Roth, J. "The colloidal gold marker system for light and electron microscopic cytochemistry" in Bullock, G. R. and Petrusz, P., eds., "Techniques in Immunocytochemistry", vol. 2, New York, Academic Press, 1983, 216-284.

After cooling the previously described gold sol solution to room temperature, the pH value of the gold sol is adjusted to pH 8.0 with 0.2 M potassium carbonate solution. A dialysed solution of monoclonal IgG antibody to digoxin (source: Roche Diagnostics GmbH, Mannheim, Germany) was added to the gold sol. The volume ratio of IgG solution to colloidal gold solution was 1:10. After 30 minute stirring at room temperature the gold conjugate was saturated by adding a highly concentrated bovine serum albumin solution (final concentration in the conjugate solution: 1 mg/ml).

The gold conjugate was concentrated to an optical density of typically 20 (absorbance at 525 nm and 1 cm light path) by ultrafiltration against a 20 mM Tris buffer pH 8.0. The conjugate solution was finally adjusted to a final concentration of 100 µM Brij® and 0.05 percent by weight sodium azide.

B. Preparation of a Conjugate Composed of Digoxin and Polyclonal Antibody to Benzodiazepine Sheep are immunized as described in example 1 of EP-A 0726275 with 7-chloro-3-[2-(N-maleinimido)ethyl]oxy-1-methyl-5-phenyl-1H-1,4-benzodiazepine-2-(3H)-one the synthesis of which is known from example 3 of EP-A 0726275. 100 ml serum of a sheep immunized in this manner containing ca. 6.5 g protein was firstly treated with 1.5 g aerosil (1 hour at room temperature) and centrifuged. The supernatant was decanted and adjusted with ammonium sulfate to 1.9 M. This precipitates the IgG. The precipitate was centrifuged and the supernatant was decanted. The precipitate was taken up in weak PBS buffer pH 7 and dialysed. The dialysate was negatively purified over 100 ml DEAE Sephadex ff. In this process impurities remained on the column and the immunoglobulin ran through. The eluate was collected (detection at 280 nm) and rebuffered in PBS buffer pH 7.4 for the immunosorption. Yield 3.5 g IgG in 90 ml solution.

3.5 g IgG in 90 ml from the DEAE purification was circulated by pump over 50 ml immunoadsorber (Spherosil, to which a polyhapten composed of Temazepam on rabbit IgG (see example 1D) is bound). In this process the immunospecific IgGs were bound and all other proteins ran through. It was re-washed with PBS buffer. The bound IgG was washed further with two column volumes of sodium chloride/TWEEN 20™ and two column volumes of 30 mM sodium chloride. Then it was eluted stepwise. The first step is elution with 3 mM hydrochloric acid at 4 to 8° C., the second step is elution with 1 M propionic acid at 4 to 8° C. and the third step is elution with 1 M propionic acid at room temperature. The eluates were immediately dialysed against ice water. The eluates were additionally dialysed against 1 mM acetic acid and, after concentration, they were filtered and lyophilized. The yield was approximately 300 mg polyclonal IgG antibody to benzodiazepinie.

The polyclonal antibodies prepared in this manner were dissolved in water to a concentration to 12 mg antibody per ml. They were re-buffered with 1.5 ml 1 M potassium phosphate buffer pH 8.3 to 0.1 M potassium phosphate and adjusted to 10 mg antibody per ml. Digoxin succinimide ester was dissolved in DMSO to a concentration of 10 mg/ml and a 6-fold molar excess of the digoxin derivative was pipetted at 4° C. into the antibody solution. It was allowed to react for three hours at 4° C. Subsequently it was dialysed against a 50-fold volume of 20 mM Tris pH 8 and against a 50-fold volume of 50 mM sodium chloride for at least foul hours in each case.

C. Preparation of Polymerized Streptavidin

Polymerized streptavidin was prepared as described in examples 1c and 1d of EP-B 0331127, which is incorporated herein by reference.

D. Preparation of Biotinylated Temazepam Polyhapten 1.2 g unspecific lyophilized polyclonal rabbit IgG was dissolved in 40 ml potassium phosphate buffer pH 8.5 and after centrifugation the clear supernatant was decanted. The supernatant contained 950 mg protein. 12.4 mg S-acetylthiopropionic acid succinimidyl ester dissolved in 1.24 ml DMSO was added to the rabbit IgG solution and stirred for two hours at room temperature. The reaction was stopped by addition of 0.5 ml 1 M lysine solution and dialysed against triethylammonium citrate/EDTA solution pH 6.5.

After dialysis the activated rabbit immunoglobulin was deacetylated for two hours at 4° C. with 1 ml 1 M ammonium hydroxide Solution per 25 ml immunoglobulin Solution at pH 6.5.

For 950 ng deacetylated activated rabbit IgG in 50 ml buffer, 10.8 mg Temazepam (prepared according to example 3 in EP-A 0726275) was dissolved in 1.08 ml DMSO and added to the deacetylated activated rabbit immuoglobulin solution. After two hours at 4° C. the reaction was stopped with 2 ml 0.1 M cysteine and the solution was incubated for 30 minutes with 2 ml 0.5 M iodoacetamide and subsequently dialysed for 30 minutes at room temperature against triethanolamine buffer pH 8.5.

24 mg biotin-succinimidyl ester dissolved in 2.4 ml DMSO was added to 950 mg of the Temazepam polyhapten prepared in this manner and stirred for two hours at room temperature. Subsequently it was intensively dialysed against weak acetic acid (10 to 1 mM). After dialysis the dialysate was adjusted with 1 M sodium acetate pH 4.2 to 20 mM sodium acetate pH 4.2 and purified by column chromatography over tris-acryl-carboxymethylcellulose.

E. Preparation of Analytical Elements According to FIG. 1

Two analytical elements according to the invention were prepared with different conjugate zones (2).

The following zones according to FIG. 1 were glued onto Support foil (5) of 5 mm width.

Sample application zone (1): Polyester fleece from the Binzer Company, Hatzfeld, Germany. A pure polyester fleece which is strengthened with 10% Kuralon, has a thickness of 1.0 to 1.2 mm and an absorptive capacity of 1800 ml/m$^2$.

Conjugate zone (2): A mixed fleece composed of 80 parts polyester and 20 parts synthetic wool strengthened with 20 parts Kuralon having a thickness of 0.32 mm and an absorptive capacity of 500 ml/m$^2$ was impregnated with one of the following solutions and dried:

Impregnation Solution A

A mixture of 1 ml of the gold conjugate A prepared in "A" diluted in Hepes buffer (200 mM, pH 7.5) to an antibody concentration of 0.3 nmol/ml and 1 ml of the digoxin conjugate prepared in "B" diluted in Hepes buffer (200 mM, pH 7.5) to a digoxin concentration of 2 nmol/ml is incubated for one hour at room temperature. Subsequently it is impregnated in the fleece.

Impregnation Solution B

A mixture of 1 ml of the gold conjugate B prepared in "A" diluted in Hepes buffer (200 mM, pH 7.5) to an antibody concentration of 1.4 nmol/ml and 1 ml of the digoxin conjugate prepared in "B" diluted in Hepes buffer (200 mM, pH 7.5) to a digoxin concentration of 2 nmol/ml is incubated for one hour at room temperature. Subsequently it is impregnated in the fleece.

Capture zone (3): A fleece composed of 100% linters, strengthened with two percent by weight Etadurin with a thickness of 0.41 mm and an absorptive capacity of 386 ml/m$^2$ is impregnated with a Solution of 200 mg/l of the polymerized streptavidin prepared in C in 50 mmol/l sodium phosphate pH 8.0 and subsequently dried. The preimpregnated fleece is subsequently impregnated again with a solution of 300 mg/l of the biotinylated Temazepam polyhapten prepared in D. in 50 mmol/l sodium phosphate pH 8.0 and dried.

Detection zone (4): A fleece of 100% linters, strengthened with two percent by weight Etadurin with a thickness of 0.35 mm and an absorptive capacity of 372 ml/m$^2$ is used.

F. Test Procedure

In order to determine benzodiazepinie with an element prepared in "E", the test strip is dipped for ca. 5 seconds in the liquid to be examined Such that the sample application zone (1) is located about three quarters below the liquid level. Afterwards the element is placed horizontally on a non-absorbent support. When the liquid front has completely wetted the detection zone (4) (usually after two minutes at most in the case of aqueous solutions) a pink colouration indicates the presence of benzodiazepines in the sample to be examined. When no substances are present which are recognized by the digoxin-labelled antibody the detection field remains white. The intensity of the pink colour correlates with the analyte concentration. A colour table simplifies the assignment.

Color field (FF) 0: negative, no analyte
Color field (PF) 1: positive, light pink
Color field (FF) 2: strongly positive, strong red color Results Table

|  | Aqueous solution containing Bromazepam | | Urine containing Bromazepam | | |
| --- | --- | --- | --- | --- | --- |
|  | 0 ng/ml | 100 ng/ml | 0 ng/ml | 50 ng/ml | 100 ng/ml |
| gold conjugate A | FF 0 | FF 1-2 | FF 0 | FF 0-1 | FF 1-2 |
| gold conjugate B | FF 0 | FF 2 | — | — | — |

What is claimed is:

1. A method for the determination of the presence of an analyte in a sample, the method comprising the steps of:
   providing an element comprising a sample application zone, a detection zone located downstream from the sample application zone and being the last zone of the element that allows liquid transport, the detection zone being devoid of a binding reagent that would enable detection of the analyte, a zone containing immobilized analyte or analyte analogue located between the sample application zone and the detection zone, a conjugate impregnated in a matrix material located upstream of the zone containing immobilized analyte or analyte analogue, the conjugate can be detached from the matrix material by liquid and comprises a first bioaffine binding partner capable of a specific binding reaction with the analyte to be determined and a first detectable label, wherein the first detectable label is a low molecular organic molecule, and a universal conjugate, located upstream of the zone containing immobilized analyte or analyte analogue, which can be detached by liquid and comprises a second bioaffine binding partner and a visually detectable label, the second bioaffine binding partner is capable of a specific binding reaction with the first detectable label, wherein the visually detectable label is a direct visually detectable label formed to carry out the determination of the analyte in the detection zone, wherein the matrix and the zones are made form liquid permeable transport materials,
   contacting the sample application zone of the element with the sample,
   allowing the sample and any analyte present therein to migrate from the sample application zone to contact and react analyte present in the sample with the conjugate impregnated in the matrix material and the universal conjugate to form a detection complex,
   determining the presence of the detection complex in the detection zone of the element, and
   relating the presence of the complex in the detection zone with the presence of the analyte in the sample.

2. The method of claim 1 wherein the determining step includes optically observing the detection complex.

3. The method of claim 2 wherein the detection complex is detected by visual coloration.

4. The method of claim 1 further comprising the step of adding an elution agent to the element to transport the sample toward the detection zone.

5. The method of claim 1 wherein the first detectable label is digoxigenin or digoxin.

6. The method of claim 5 wherein the second bioaffine binding partner is an antibody to digoxigenin or digoxin.

7. The method of claim 1 wherein the second bioaffine binding partner is an antibody to digoxigenin or digoxin.

8. The method of claim 1 wherein the visually detectable label is metal particles or latex particles.

9. The method of claim 8 wherein the visually detectable label is gold particles.

* * * * *